United States Patent
Garault et al.

(10) Patent No.: US 9,387,229 B2
(45) Date of Patent: Jul. 12, 2016

(54) **REUTERIN-PRODUCING *LACTOBACILLUS BREVIS***

(75) Inventors: Peggy Garault, Montlhery (FR); Gaelle Quere, Villebon sur Yvette (FR); Raphaelle Bourdet-Sicard, Palaiseau (FR)

(73) Assignee: Compagnie Gervais Danone, Paris (FR)

( * ) Notice: Subject to any disclaimer, the term of this patent is extended or adjusted under 35 U.S.C. 154(b) by 0 days.

(21) Appl. No.: 14/361,565

(22) PCT Filed: Nov. 30, 2011

(86) PCT No.: PCT/IB2011/055391
§ 371 (c)(1),
(2), (4) Date: Jul. 3, 2014

(87) PCT Pub. No.: WO2013/079992
PCT Pub. Date: Jun. 6, 2013

(65) Prior Publication Data
US 2014/0341855 A1    Nov. 20, 2014

(51) Int. Cl.
| | |
|---|---|
| *A61K 35/747* | (2015.01) |
| *C12N 1/21* | (2006.01) |
| *C12N 15/00* | (2006.01) |
| *C12R 1/24* | (2006.01) |
| *A23L 1/30* | (2006.01) |
| *A23C 9/123* | (2006.01) |
| *A61K 31/357* | (2006.01) |
| *C12P 17/06* | (2006.01) |

(52) U.S. Cl.
CPC ............. *A61K 35/747* (2013.01); *A23C 9/1234* (2013.01); *A23L 1/3014* (2013.01); *A61K 31/357* (2013.01); *C12P 17/06* (2013.01); *C12R 1/24* (2013.01); *A23V 2002/00* (2013.01); *A23Y 2220/13* (2013.01)

(58) Field of Classification Search
None
See application file for complete search history.

(56) References Cited

U.S. PATENT DOCUMENTS

2007/0148749 A1* 6/2007 Yasuda et al. ................. 435/158
2008/0254011 A1* 10/2008 Rothschild et al. ........ 424/93.45

OTHER PUBLICATIONS

Bauer et al., "Influence of environmental parameters on production of the acrolein precursor 3-hydroxypropionaldehyde by Lactobacillus reuteri DSMZ 20016 and its accumulation by wine lactobacilli," International Journal of Food Microbiology, 137: 28-31 (2010).
Morita et al., "Comparative Genome Analysis of Lactobacillus reuteri and Lactobacillus fermentum Reveal a Genomic Island for Reuterin and Cobalamin Production," DNA Research, 15: 151-161 (2008).
Schutz et al., "Anaerobic Reduction of Glycerol to Propanediol-1.3 by Lactobacillus brevis and Lactobacillus buchneri," Systematic and Applied Microbiology, 5: 169-178 (1984).

* cited by examiner

*Primary Examiner* — Maria Marvich
(74) *Attorney, Agent, or Firm* — Morgan, Lewis & Bockius LLP

(57) ABSTRACT

The invention relates to reuterin-producing strains of *Lactobacillus brevis*. These strains are useful in particular for the treatment or the prevention of conditions resulting from *Helicobacter pylori* infection.

9 Claims, 2 Drawing Sheets

SEQUENCE LISTING

<160> NUMBER OF SEQ ID NOS: 6

<210> SEQ ID NO 1
<211> LENGTH: 23
<212> TYPE: DNA
<213> ORGANISM: Artificial Sequence
<220> FEATURE:
<223> OTHER INFORMATION: PCR primer

<400> SEQUENCE: 1
gcrgcyttsa tatctksaac cat                                                 23

<210> SEQ ID NO 2
<211> LENGTH: 26
<212> TYPE: DNA
<213> ORGANISM: Artificial Sequence
<220> FEATURE:
<223> OTHER INFORMATION: PCR primer

<400> SEQUENCE: 2
gcmtaygcwg aaaccatttc agttta                                              26

<210> SEQ ID NO 3
<211> LENGTH: 20
<212> TYPE: DNA
<213> ORGANISM: Artificial Sequence
<220> FEATURE:
<223> OTHER INFORMATION: PCR primer

<400> SEQUENCE: 3
actcctacgg gaggcagcag                                                     20

<210> SEQ ID NO 4
<211> LENGTH: 22
<212> TYPE: DNA
<213> ORGANISM: Artificial Sequence
<220> FEATURE:
<223> OTHER INFORMATION: PCR primer

<400> SEQUENCE: 4
gtattaccgc ggctgctggc ac                                                  22

<210> SEQ ID NO 5
<211> LENGTH: 22
<212> TYPE: DNA
<213> ORGANISM: Artificial Sequence
<220> FEATURE:
<223> OTHER INFORMATION: PCR primer

<400> SEQUENCE: 5
caatagcaat caagtggctt tg                                                  22

<210> SEQ ID NO 6
<211> LENGTH: 18
<212> TYPE: DNA
<213> ORGANISM: Artificial Sequence
<220> FEATURE:
<223> OTHER INFORMATION: PCR primer

<400> SEQUENCE: 6
gcgcgcttcc acattagc                                                       18

REUTERIN-PRODUCING *LACTOBACILLUS BREVIS*

SEQUENCE LISTING SUBMISSION VIA EFS-WEB

A computer readable text file, entitled "045636-5262-SequenceListing.txt" created on or about May 29, 2014, with a file size of about 2 kb contains the sequence listing for this application and is hereby incorporated by reference in its entirety.

The present invention relates to reuterin-producing strains of *Lactobacillus brevis* (*L. brevis*) and to their uses, in particular for the treatment or the prevention of *Helicobacter pylori* (*H. pylori*) infection and conditions resulting thereof.

Reuterin (3-hydroxypropionaldehyde, 3-HPA) is an antimicrobial compound which was initially identified as produced by a number of strains of *Lactobacillus reuteri* (*L. reuteri*) when cultivated under anaerobic conditions in the presence of glycerol (TALARICO & DOBROGOSZ, Antimicrob Agents Chemother, 33, 674-9, 1989). The conversion of glycerol to reuterin is catalysed by a cobalamin-dependent glycerol dehydratase (Gld; EC 4.2.1.30), which is composed of three subunits (C, D and E, or $\alpha$, $\beta$ and $\gamma$ respectively). The existence of the Glycerol dehydratase (GDA) pathway has also been reported in *lactobacilli* species other than such as *Lactobacillus collinoides*, *Lactobacillus brevis*, and *Lactobacillus hilgardii*. For all species, the existence of this pathway appears to vary from strain to strain, depending on the presence of a gene encoding glycerol dehydratase or diol dehydratase (CADIEUX et al., Appl Environ Microbiol, 74, 4645-9, 2008; SAUVAGEOT et al., FEMS Microbiology Letters, 209, 69-74, 2002; CLAISSE and LONVAUD-FUNEL, Journal of Food Protection, 64, 833-837, 2001). In most of bacteria metabolizing glycerol through the GDA pathway, reuterin is normally a metabolic intermediate which is subsequently reduced intracellularly to 1,3-propanediol, (1,3-PD) which is excreted in the extracellular medium. Only some of the strains possessing glycerol- or diol dehydratase are able to accumulate reuterin in the culture medium. Most of these reuterin-accumulating strains belong to the species *L. reuteri*. However some strains able to accumulate reuterin extracellularly, generally to a lesser extent than *L. reuteri*, have been reported in other *lactobacilli* species: *Lactobacillus coryniformis* (MARTIN et al., Int J Food Microbiol, 104, 267-77, 2005), *Lactobacillus collinoides* (GARAI-IBABE et al., International Journal of Food Microbiology 121, 253-261, 2008; SAUVAGEOT et al., International Journal of Food Microbiology, 55, 167-170, 2000), and *Lactobacillus hilgardii* (PASTERIS and STRASSER DE SAAD, J. Agric. Food Chem., 57 (9), 3853-3858, 2009). More recently, one strain of *Lactobacillus brevis* and one strain of *Lactobacillus pentosus* able to accumulate reuterin extracellularly (to concentrations however 10-folds lower than *L. reuteri*) have been described (BAUER et al., International Journal of Food Microbiology, 137, 28-31, 2010).

Reuterin has a broad spectrum of anti-microbial activity on potentially harmful micro-organisms. Reuterin can inhibit the growth of yeast, fungi, protozoa, and various harmful bacteria at concentrations four to five lower than those necessary to inhibit the growth of lactic acid bacteria. Due to this selective anti-microbial activity of reuterin, which allows it to destroy a variety of pathogenic micro-organisms while not harming the beneficial lactic acid bacteria of the intestinal flora, it has been proposed to use it for treating various digestive disorders.

Several *L. reuteri* strains have been considered as candidate probiotics, in particular because of their protective effects against pathogens such as *Salmonella enterica*, *Escherichia coli*, *Clostridium difficile*, and *Helicobacter pylori* (CLEUSIX et al., BMC Microbiol, 7, 101, 2007; SPINLER et al., Anaerobe, 14, 166-71, 2008; FRANCAVILLA et al., *Helicobacter*, 13, 127-34, 2008; PCT WO 2004/031368). These effects have been linked at least in part to the production of reuterin.

Among the pathogenic microorganisms of the gastrointestinal tract, *Helicobacter pylori* has been a focus of increasing interest in the past years. It is a Gram-negative spiral-shaped bacteria that colonizes the human gastric mucus layer of more than 50% of the world's population. While the majority of individuals infected with *H. pylori* is asymptomatic although their gastric epithelium show sign of inflammation, 15% to 20% of *H. pylori* infected subjects will develop diseases. *H. pylori* is the major causative agent of peptic ulcer diseases, chronic active gastritis, atrophy, metaplasia, dysplasia, gastric cancer and gastric mucosa associated lymphoid tissue (MALT) lymphoma (see for review (FOX & WANG, J Clin Invest, 117, 60-9, 2007; POLK & PEEK, Nat Rev Cancer, 10, 403-14)).

The standard treatment in patients infected with *H. pylori* is two antibiotics plus a PPI (proton pump inhibitor) treatment, so called triple therapy. However, *H. pylori* eradication rate following triple therapy is dropping down because of antibiotic resistance or poor compliance. Further, despite several assays, there is no effective vaccine available on the market yet.

The use of probiotics has been proposed as alternatives or complements to triple therapy for treating or preventing *H. pylori*. As indicated above, these probiotics include in particular *L. reuteri* due in particular to its anti-microbial properties. Some strains of other *lactobacilli* species have also been proposed as potentially useful for the management of *H. pylori* infection. For instance, SIMOVA et al. (J Appl Microbiol, 106, 692-701, 2009), disclose a *Lactobacillus delbrueckii* strain (BB 18) producing an inhibitory peptide (bacteriocin) and strongly inhibiting *H. pylori*. LINSALATA et al. (*Helicobacter*, 9, 165-72, 2004), studied the effects of a particular *L. brevis* strain (CD2) with a high arginine deiminase activity on *H. pylori* survival in the human gastric mucosa. They found a reduction of intragastric *H. pylori* load, and suggested that it might be due to the elevated arginine deiminase activity, which would deprive *H. pylori* of arginine, and inhibit their growth and proliferation.

The inventors have now isolated a strain of *Lactobacillus brevis* having the ability to produce reuterin and accumulate it in sufficient quantity to have anti-microbial activity on a wide range of strains of *H. pylori*.

A strain "able to accumulate reuterin" or a "reuterin-accumulating" strain is defined herein as a strain which able to produce reuterin and secrete it extracellularly.

Therefore, an object of the present invention is this strain of *L. brevis* which has been deposited according to the Budapest Treaty with the CNCM (Collection Nationale de Cultures de Microorganismes, 25 rue du Docteur Roux, Paris) on 3 Feb. 2011, under accession number CNCM I-4431, which would become irrevocably available to the public upon grant of a patent.

Besides its ability to produce and accumulate reuterin, this strain has the following characteristics:

Morphology: rod-shaped bacteria with homogen coloration, grouped in small chains;

Metabolism: heterofermentative;

Fermentation of the following sugars (results obtained on an Api 50 CH strip—API MRS medium at 37° C. for 48 h): L-Arabinose, D-Ribose, D-xylose, D-Glucose, D-Fructose, D-Maltose, D-Melibiose, Potassium Gluconate, Potassium 5-Cétogluconate.

The present invention also encompasses *L. brevis* reuterin-accumulating strains derived by mutagenesis or by genetic transformation of the CNCM I-4431 strain, provided that they retain the antimicrobial properties and the reuterin-producing ability of this parent strain. They may be strains in which one or more of the endogenous genes of the CNCM I-4431 strain has (have) been mutated, for example so as to modify some of its metabolic properties (e.g. the ability of this strain to metabolize sugars, its resistance to intestinal transit, its resistance to acidity, or its post-acidification). They may also be strains resulting from genetic transformation of the CNCM I-4431 strain with one or more gene(s) of interest, making it possible, for example, to confer additional physiological characteristics on said strain, or to express proteins of therapeutic or vaccine interest, which it is desired to administer by means of said strain.

These strains can be obtained from the CNCM I-4431 strain by means of the conventional techniques for random or site-directed mutagenesis and genetic transformation of *lactobacilli*, such as those described, for example, by GURY et al. (Arch Microbiol., 182, 337-45, 2004) or by VELEZ et al. (Appl Environ Microbiol., 73, 3595-3604, 2007), or by means of the technique known as "genome shuffling" (PATNAIK et al. Nat Biotechnol, 20, 707-12, 2002; WANG Y. et al., J Biotechnol., 129, 510-15, 2007).

A subject of the present invention is also a method for obtaining a reuterin-accumulating strain of *Lactobacillus brevis*, comprising a step of mutagenesis or genetic transformation of the strain CNCM I-4431.

The *L. brevis* strains of the invention can be used for producing reuterin. Therefore, another subject of the present invention is a method for producing reuterin comprising the steps of:

culturing *L. brevis* strain of the invention as defined above, preferably the strain CNCM I-4431, in the presence of glycerol and recovering the reuterin produced by the culture.

A subject of the present invention is also a composition comprising a *L. brevis* strain of the invention, preferably the strain CNCM I-4431.

In the composition of the invention, said strain can be used in the form of whole bacteria, preferably living bacteria.

The compositions of the invention can be in any form suitable for administration, in particular oral administration. This includes for instance solids, semi-solids, liquids, and powders. Liquid composition are generally preferred for easier administration, for instance as drinks.

The composition can comprise at least $10^5$ cfu, preferably at least $10^6$ cfu, per g dry weight, of a *L. brevis* strain of the invention.

The composition can further comprise other strains of bacteria, in particular probiotic strain(s), such as *Lactobacillus, Bifidobacterium, Streptococcus* or *Lactococcus* strain(s).

The composition may typically comprise $10^5$ to $10^{13}$ colony forming units (cfu), preferably at least $10^6$ cfu, more preferably at least $10^7$ cfu, still more preferably at least $10^8$ cfu, and most preferably at least $10^9$ cfu per g dry weight of the composition of the *L. brevis* strain of the invention. In the case of a liquid composition, this corresponds generally to $10^4$ to $10^{12}$ colony forming units (cfu), preferably at least $10^5$ cfu, more preferably at least $10^6$ cfu, still more preferably at least $10^7$ cfu, and most preferably at least $10^9$ cfu/ml.

The composition can be a nutritional composition, including food products, food supplements and functional food. A "food supplement" designates a product made from compounds usually used in foodstuffs, but which is in the form of tablets, powder, capsules, portion or any other form usually not associated with aliments, and which has beneficial effects for one's health. A "functional food" is an aliment which also has beneficial effects for one's health. In particular, food supplements and functional food can have a physiological effect—protective or curative—against a disease, for example against a chronic disease.

The nutritional composition according to the invention also includes a baby food, an infant milk formula or an infant follow-on formula. Preferably the present composition is a nutraceutical or a pharmaceutical product, a nutritional supplement or medical food.

The composition can be a dairy product, preferably a fermented dairy product. The fermented product can be present in the form of a liquid or present in the form of a dry powder obtained by drying the fermented liquid. Examples of dairy products include fermented milk and/or fermented whey in set, stirred or drinkable form, cheese and yoghurt.

The fermented product can also be a fermented vegetable, such as fermented soy, cereals and/or fruits in set, stirred or drinkable forms.

In a preferred embodiment, the fermented product is a fresh product. A fresh product, which has not undergone severe heat treatment steps, has the advantage that bacterial strains present are in the living form.

A subject of the present invention is also a *L. brevis* strain of the invention, preferably the strain CNCM I-4431, or a composition of the invention for use as a medicament. The *L. brevis* strains and compositions of the invention are particularly useful for treating or preventing a *H. pylori* infection.

A subject of the present invention is also the use of a *L. brevis* strain of the invention, preferably the strain CNCM I-4431, or a composition of the invention as a medicament, or for the manufacture of a medicament, preferably a medicament for treating or preventing *H. pylori* infection.

A subject of the present invention is also a method for treating or preventing *H. pylori* infection in a subject in need thereof, said method comprising administering to said subject a therapeutically effective amount of a *L. brevis* strain of the invention, preferably the strain CNCM I-4431, or of a composition of the invention.

The present invention also encompasses a method for the manufacture of a medicament, preferably a medicament for treating or preventing *H. pylori* infection, said method comprising incorporating a *L. brevis* strain as defined above, preferably the strain CNCM I-4431, into at least one pharmaceutically acceptable diluent, carrier or excipient.

Methods for diagnosing a *H. pylori* infection are known in the art. By way of example, diagnosis of a *H. pylori* infection can be made by checking by a blood antibody test, a stool antigen test or the carbon urea breath test. It can also be made by biopsy under endoscopy followed by an urease test, a histological examination or a microbial culture.

Symptoms or diseases associated with *H. pylori* infection are in particular stomach ache, heartburn, acid reflux, abdominal pain, regurgitation, vomiting, belching, flatulence, nausea, esophagitis, gastritis such as chronic active gastritis, peptic ulcer diseases, atrophy, metaplasia, dysplasia, gastric cancer and gastric mucosa associated lymphoid tissue (MALT) lymphoma.

The present invention will be understood more clearly from the further description which follows, which refers to examples illustrating the antimicrobial immunomodulatory and anti-infective properties of the CNCM I-4431 strain as well as to the appended figures.

EXAMPLE 1

Figure 1:
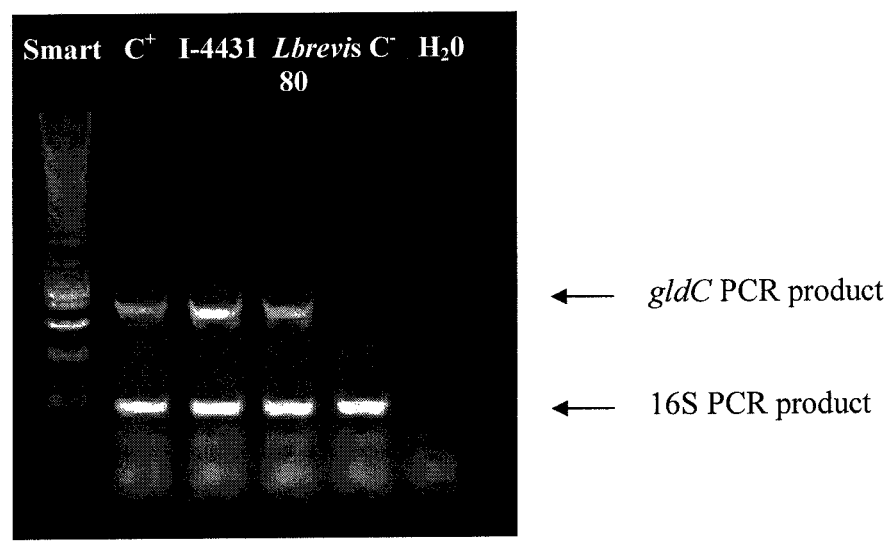
FIG. 1 shows the results of the PCR reaction of *Lactobacillus brevis* strains for gldC sequence. Upper band at 728 by represents the expected product using the gldC gene-specific primers. Lower band at 201 by represents the expected product using the 16S rRNA gene-specific primers (positive PCR control); Smart: DNA SMART Ladder (Eurogentec); C+: PCR result obtained from DNA control from the positive gldC strain *Lactobacillus reuteri* ATCC 55730; I-4431: PCR result obtained from DNA from the *L. brevis* strain CNCM I-4431; *L. brevis* 80: PCR result obtained from DNA from the *L. brevis* 80 C−: PCR result obtained from DNA control from a gldC negative strain of *Streptococcus thermophilus*; $H_2O$: PCR result obtained from sterile water.

In Vitro Inhibition of the Growth of *H. pylori* Strains by the strain *L. Brevia* CNCM I-4431

Material & Methods
*Lactobacillus brevis* Strains:
  *L. brevis* CNCM I-4431
  *L. brevis* 80: A conventional strain of *L. brevis*

*Helicobacter pylori* Strains:
Three *H. pylori* reference strains were used as well as five clinical isolates.
Reference Strains:
  26695: described in TOMBS et al. (Nature 388, 539-547, 1997);
  HPAG1: described in OH et al. (Proc Natl Acad Sci USA., 103, 9999-10004, 2006);
  TN2GF4: isolated in Japan from a patient with gastric ulcer and adapted to Mongolian gerbil (strain described in WATANABE, et al. Gastroenterol 1998; vol 115, pp 642-648)
Clinical Isolates:
  CR113 and CR114: strains isolated from human precancerous gastric lesions biopsies;
  Axcan 342 and Axcan 374: strains isolated respectively from a patient with gastritis and a patient with esophagitis included in clinical study testing a quadruple therapy for eradication *H. pylori* (MALFERTHEINER et al., Lancet, 377, 905-913, 2011).
  GC3C: strain isolated from a patient with a gastric cancer.
Method:
*L. brevis* stains were grown in MRS Broth (pH 6,2) for 17 h. The bacterial suspensions were neutralized at pH 6,8 with a solution of KOH.

*H. pylori* strains were grown for 48 h in Brucella Broth until obtaining a turbidity equivalent to the Mac Farland 4 standard. The bacterial suspensions were spread onto the surface of Mueller Hinton Agar plates supplemented with 10% (v/v) sheep blood, enriched by Polyvitex supplement at 1% (v/v) (Biomerieux) and in the same medium with glycerol to a final concentration of 100 mM to allow the production of reuterin.

Sterile paper discs were applied on the surface of the plates. Then, 5 μL of the neutralized *L. brevis* suspension were applied on each paper disc. The plates were incubated at 37° C. under micro-aerophilic atmosphere (Ruskin Microaerophilic gas sorter, resulting in 5% $O_2$, 10% $CO_2$, and 85% $N_2$) for 72 h to 96 h.

To assess the effect of the *L. brevis* suspension on the growth of *H. pylori* strain, the width of rings of growth inhibition around the paper disks were measured.
Results
The results are shown in Table I below.

TABLE I

|  | 26695 | HPAG1 | TN2GF4 | CR113 | CR114 | Axcan 342 | Axcan 374 | GC3C |
|---|---|---|---|---|---|---|---|---|
| *L. brevis* I-4431 Ring of inhibition in mm | 30 | 30 | 15 | 15 | 10 | 30 | 11 | 30 |
| *L. brevis* I-4431 Ring of inhibition in mm (without glycerol) | 0 | 0 | 0 | 0 | 0 | 0 | 0 | 0 |
| *L. brevis* 80 Ring of inhibition in mm | 0 | 0 | 0 | 15 | 0 | 0 | 0 | 40 |
| *L. brevis* 80 Ring of inhibition in mm without glycerol | 0 | 0 | 0 | 0 | 0 | 0 | 0 | 0 |

These results show that while *L. brevis* 80 has inhibitory properties on only two strains of *H. pylori* tested, *L. brevis* I-4431 inhibits the growth of 8 of the 8 strains of *H. pylori* tested. These inhibitory properties appear to be linked to the accumulation of reuterin, since they are only observed with *L. brevis* cultures grown in presence of glycerol.

EXAMPLE 2

PCR Screening of the GLDC Gene

Material & Methods

The presence in *L. brevis* CNCM I-4431 of the gene encoding the large subunit of glycerol dehydratase (GldC)—the enzyme responsible for reuterin production—was tested following the method described by CADIEUX et al. (2008, cited above).

Briefly, total DNA was isolated from each tested bacterial strain.

As a positive control (C+), the reuterin-producing strain *L. reuterii* ATCC 55730 was used. As a negative control (C−), a strain of a non-reuterin-producing species (*Streptococcus thermophilus*) was used.

Amplification of a fragment of the gene encoding the large subunit of Gld (gldC) was carried out with the degenerate primers:

GDCRev: GCRGCYTTSATATCTKSAACCAT (SEQ ID NO: 1) and
GDCFor: GCMTAYGCWGAAACCATTTCAGTTTA (SEQ ID NO: 2), both described in CADIEUX et al. The expected size of the amplified gldC fragment is 728 bp.

As a positive PCR reaction control, a fragment of the 16S rRNA gene was also amplified from all samples by using the eubacterial primers:

16SFor: ACTCCTACGGGAGGCAGCAG (SEQ ID NO: 3) and
16SRev: GTATTACCGCGGCTGCTGGCAC (SEQ ID NO: 4), both also described in CADIEUX et al.

The expected size of the amplified 16S rRNA fragment is 201 bp.

Results

The results of the PCR reaction are shown in FIG. 1. The strain *L. brevis* CNCM I-4431, *L. brevis* 80 as well as the (C+) reuterin-producing strain *L. reuterii* ATCC 55730 were positive for the expected 728-bp product. Accordingly, the strain *L. brevis* CNCM I-4431 contains the gldC gene, allowing it to produce reuterin.

EXAMPLE 3

Effect of *L. Brevis* CNCM I-4431 Infection by *H. Pylori* on *C. Elegans* Model Cultures of *L. brevis* and *H. pylori*

*L. brevis* strain CNCM I-4431 was grown in MRS Broth as disclosed in Example 1.

Strain NCTC11637 (ATCC $43504^T$) of *H. pylori* was grown in BHI medium (Oxoid) containing 5% (v/v) horse blood (Oxoid).

Supernatants were separated from cells by centrifugation and neutralized with NaOH (1M). Then, supernatants were filtrated (0.22 μm) and added to the cell pellet.

In the case of *H. pylori* cultures, BHI medium containing horse blood (Oxoid) was removed by centrifugation and cells were washed with saline solution.

The NG agar plates used for *C. elegans* infection assays were prepared by addition of 100 μL of a mixture containing each LAB culture at O.D.=2.22 (including cells and supernatant) with the corresponding cells of *H. pylori* strain (O.D.=0.022). In the reference condition, were the nematodes do not fed with LAB, *H. pylori* cells where resuspended in saline solution and added to the plates.

*C. elegans* Infection Assays.

The infection assays were performed with the wild-type strain of *C. elegans* (N2). Strain NCTC11637 of *H. pylori* was used for nematode infection. Experiments were initiated with synchronized young adults (three-day nematodes) that were transferred to the different culture conditions:

NG medium+*E. coli* OP50 (control).
NG medium+*E. coli* OP50+100 μL LAB culture media (control of culture media).
NG medium+*E. coli* OP50+100 μl (*H. pylori* NCTC $11637^T$+LAB).

Worms were incubated at 25° C. during 8 days, transferring them to new plates every two days. Survival of nematode population was scored in each culture condition. After incubation period, samples of 15 worms per condition were taken, washing them with M9 buffer containing 0.1% Triton X-100. Worms were disrupted using 0.4 g of silicon carbide beads and vortex.

DNA of infected worms was isolated with a commercial kit "High Pure PCR Template Preparation Kit" (Roche), followed by a subsequent precipitation and washing process with absolute ethanol and potassium acetate 5M. Dilutions of DNA samples were used to quantify the presence of *H. pylori* in the samples by RT-PCR

RT-PCR

Primers used in this study are directed to vacA gene (NAYAK & ROSE, J Appl Microbiol, 103, 1931-41, 2007). They are named as HpylF (5' CAA TAG CAA TCA AGT GGC TTT G 3', SEQ ID NO: 5) and HpylR (5' GCG CGC TTC CAC ATT AGC 3'; SEQ ID NO: 6). The specificity was previously checked in silico by BLAST online tool and in vitro by Q-PCR with strains of *H. pylori* species, different probiotic strains and *E. coli* OP50 used for *C. elegans* feeding (see previous report of optimization). The "SYBR® Green PCR Master Mix" (Applied Biosystem) and StepOne Real-Time thermocycler (Applied Biosystem) were used. Table 2 below summarizes the optimized conditions for the Q-PCR *H. pylori* reaction.

TABLE 2

| Reaction mix | | |
|---|---|---|
| Master mix 2x | | 1x |
| Forward primer: | | 325 nM |
| Reverse primer: | | 325 nM |
| Thermal cycling | | |
| Holding stage | 50° C. | 2 min. |
|  | 95° C. | 10 min. |
| Cycling stage (x40) | 95° C. | 15 s. |
|  | 60° C. | 1 min. |

DNA for standard curve was prepared by quantification of *H. pylori* DNA by spectrophotometry (A260). The number of the corresponding genomes was calculated as follows:

Genome Number=DNA (g)×NA/Mm
*H. pylori* genome size=1.6 Mpb
NA=6.023×1023
Genome Number=DNA(g)×6.023×1023/1.6×106×2×309

Standard curve was performed using four ten-fold dilutions of DNA.

Figure 2:
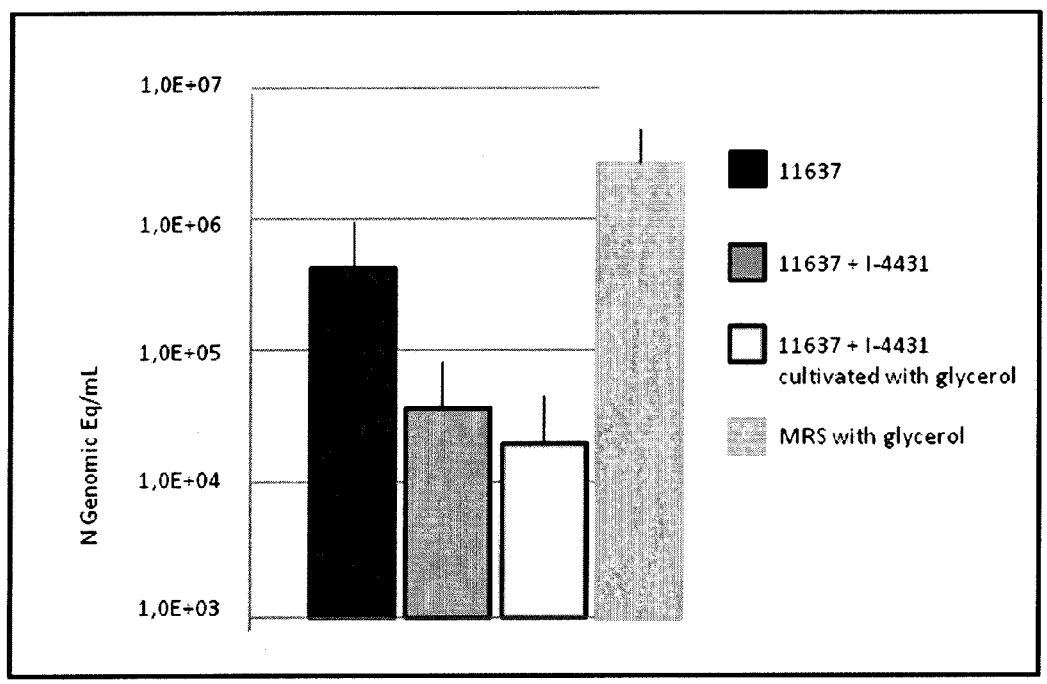
FIG. 2 shows the quantification of *H. pylori* (strain NTCTC11637) in *C. elegans* after ingestion *H. pylori* alone (black bar), of *H. pylori*+*L. brevis* I-4431 strain grown in MRS (dark grey bar), of *H. pylori*+*L. brevis* I-4431 strain grown in MRS with glycerol (white bar), or of *H. pylori*+MRS with glycerol.

The results obtained with the strain I-4431 grown in MRS or grown in MRS+glycerol are shown on FIG. 2. These results show that strain CNCM I-4431 reduces the load of *H. pylori* NCTC $11637^T$ in *C. elegans*. The reduction of infection is more important when strain I-4431 is grown in MRS+glycerol, showing that at least part of the anti-infectious effect of this strain results from reuterin production.

The invention claimed is:

1. A reuterin-accumulating *Lactobacillus brevis* strain that is the *Lactobacillus brevis* strain deposited with the CNCM (Collection Nationale De Cultures De Microorganismes) under Accession number I-4431.

2. A method of producing reuterin comprising the steps of:
 (a) culturing the *Lactobacillus brevis* strain of claim 1 under conditions sufficient to produce reuterin and
 (b) recovering the reuterin produced by the culture in step (a).

3. A nutritional composition comprising the *Lactobacillus* strain of claim 1.

4. The composition according to claim 3, comprising at least $10^5$ cfu, per gram dry weight, of the *Lactobacillus brevis* strain.

5. The composition of claim 3, wherein the composition is a dairy product.

6. The composition of claim 3, wherein the composition is a fermented dairy product.

7. A pharmaceutical composition comprising the *Lactobacillus brevis* strain of claim 1.

8. A method of treating an *H. pylori* infection in a subject in need thereof comprising administering to the subject the pharmaceutical composition according to claim 7 in an amount effective to treat the *H. pylori* infection.

9. The method of claim 8, wherein the subject is suffering from a *H. pylori* infection.

* * * * *